(12) United States Patent
Håkansson (10) Patent No.: US 6,242,202 B1
(45) Date of Patent: Jun. 5, 2001

(54) MONITORING IMMUNOTHERAPY OF MALIGNANT TUMORS

(75) Inventor: Leif Håkansson, Vikingstad (SE)

(73) Assignee: Landstinget I Ostergotland, Linkoping (SE)

( * ) Notice: Subject to any disclaimer, the term of this patent is extended or adjusted under 35 U.S.C. 154(b) by 0 days.

(21) Appl. No.: 08/952,139

(22) PCT Filed: May 10, 1996

(86) PCT No.: PCT/EP96/02006

§ 371 Date: Nov. 10, 1997

§ 102(e) Date: Nov. 10, 1997

(87) PCT Pub. No.: WO96/35948

PCT Pub. Date: Nov. 14, 1996

(30) Foreign Application Priority Data

May 12, 1995 (SE) ................................................... 9501780

(51) Int. Cl.[7] ................................................. G01N 33/574

(52) U.S. Cl. .......................... 435/7.23; 435/7.24; 436/63; 436/64; 436/813

(58) Field of Search ........................... 435/29, 7.23, 7.24; 436/63, 64, 813

(56) References Cited

FOREIGN PATENT DOCUMENTS 0 238 851    9/1987   (EP) .

OTHER PUBLICATIONS

Beaulieu, L., et al: Effects of H1 and H2 receptor agonists on nonspecific proliferative response of human peripheral blood lymphocytes. Int. Archs Allergy Appl. Immun. 79:249–252 (1986).
Berd, D., et al: "Impairment of concanavalin A–inducible suppressor activity following administration of cyclophosphamide to patients with advanced cancer." Cancer Research 44: 1275–1280 (Mar. 1984).
Blay, J.Y., et al: "Correlation between clinical response to Interleukin 2 therapy and sustained production of tumor necrosis factor." Cancer Research 50: 2371–2374 (Apr. 15, 1990).
Braun, D.P., et al: "Serial immune testing in surgically resected lung cancer patients." Cancer Immunol Immunother 15:114–120 (1983).
Broom, J., et al: "Interleukin 2 therapy in cancer: indentification of responders." Br. J. Cancer 66:1185–1187 (1992).
Catalona, W.J., et al: "Concanavalin A–activated suppressor cell activity in peripheral blood lymphocytes of urologic cancer patients." JNCI 65:553–557 (1980).
Cheema, A.R., et al: "Patients survival after chemotherapy and its relationship to in vitro lymphocyte blastogenesis." Cancer 28:851–855.
Chretien, P.B., et al: "Correlation of preoperative lymphocyte reactivity with the clinical course of cancer patients." Surg, Gynecol & Obst 136:380–384 (Mar. 1973).
Condiotti, R., et al: "The novel immunomodulator, linomide, stimulates interleukin–2–induced human natural killer (NK) cell and PHA–stimulated T cell proliferation from normal donors." Leukemia Research vol. 20, No. 1: 57–63 (1996).
Dean, J.H., et al: "The relative proliferation index as a more sensitive parameter for evaluating lymphoproliferative responses of cancer patients to mitogens and alloantigens." Int. J. Cancer 20:359–370(1977).
Duensing, S., et al: "Pretreatment natural killer antigen density correlates to clinical response in tumor patients receiving long–term subcutaneous recombinant interleukin–2 and recombinant interferon–$\alpha$." Mol. Biother. 4:170–173 (Dec. 1992).
Farinas, M.C., et al. "Contribution of monocytes to the decreased lymphoproliferative response to phytohemagglutinin in patients with lung cancer." Cancer 68:1279–1284 (Sep. 15, 1991).
De Gast, G.C., et al. "Humoral and cell–mediated immune response in patients with malignant melanoma." I. In Vitro Lymphocyte Reactivity to PHA and Antigens Following Immunization. Cancer 36:1289–1297 (Oct. 1975).
Gifford Sr., R.R., et al: "Cimetidine–induced augmentation of human lymphocyte blastogenesis by mitogen, bacterial antigen, and alloantigen." Transplantation 29:143–148 (1980).
Hilal, E.Y., et al: "Immunologic evaluation and prognosis in patients with head and neck cancer." Am J. Surg. 134:469–473 (1977).
Hoon, S.B., et al: "Suppressor cell activity in a randomized trial of patients receiving active specific immunotherapy with melanoma cell vaccine and low dosages of cyclophosphamide." Cancer Research 50:5358–5364 (Sep. 1990).
Huang, A.T., et al.: "A Prospective Study of Squamous Head and Neck Carcinoma." Cancer 59:1721–1726 (May 15, 1987).
Janssen, R.A.J., et al.: "Peripheral blood lymphocyte number and phenotype prior to therapy correlate with response in subcutaneously applied rIL–2 therapy of renal cell carcinoma." Br. J. Cancer 66:1177–1179 (1992).

(List continued on next page.)

*Primary Examiner*—Donna C. Wortman
*Assistant Examiner*—Brenda G. Brumback
(74) *Attorney, Agent, or Firm*—Merchant & Gould P.C.

(57) ABSTRACT

The present invention relates to a method of predicting the therapeutic response of a drug directed towards a cancer in a human patient using samples of blood cells taken from the patient at different times. The method comprises the steps of culturing cells from the samples in a suitable medium; adding a stimulator of proliferation and an immunomodulating drug of the cells to the culture; and assaying the proliferation of the cells in the culture; comparing the assay of proliferation with a previously made analysis demonstrating correlation between the proliferation of the cells and parameters of the therapeutic response of the drug in the human patient.

10 Claims, 8 Drawing Sheets

OTHER PUBLICATIONS

Jerrells, T.R., et al.: "Relationship between T lymphocyte levels and lymphoproliferative responses to mitogens and alloantigens in lung and breast cancer patients." Int. J. Cancer 21:282–290 (1978).

Jones, K.D., et al.: "Lymphocyte response to PHA and patient response to chemotherapy in breast cancer." Clinical Oncology 6:159–166 (1980).

Kurosu, Y., et al.: "Indomethacin enhancement of lymphocyte responses to phytohemagglutinin in breast, stomach and colorectal cancer patients." Japanese Journal of Surgery, 18(2):152–157 (1988).

Livingston, P.O., et al.: "Inhibition of suppressor–cell activity by cyclophosphamide in patients with malignant melanoma." Journal of Biological Response Modifiers 6:392–403 (1987).

Lui, V.K., et al.: "Cellular immunocompetence in melanoma: effect of extent of disease and immunotherapy." Br. J. Cancer 32:323–330 (1975).

Mantovani, G., et al.: "Interleukin 2 (IL 2) relationships with the cancer–related immunodeficiency: in vitro response to exogenous IL 2 by PHA–activated and non PHA–activated peripheral blood mononuclear cells from cancer patienst." Diagnostic and Clinical Immunology 5:104–111 (1987).

McCormick, K.J., et al.: "Indomethacin–induced augmentation of lymphoproliferative responses in patients with head and neck cancer." Cancer Immunol. Immunother. 21:226–232 (1986).

Mekori, T., et al.: "Suppression of the mitogenic response to phytohemagglutinin in malignant neoplasia: correlation with clinical stage and therapy." Journal of the National Cancer Institute, 52(1):9–12 (Jan. 1974).

Meretey, K., et al.: "Effects of histamine on the mitogenic response of human lymphocytes and its modification by cimetidine and levamisole." Agents and Actions, 11:84–88 (1981).

Nanus, D.M., et al.: "Antiproliferative and antitumor effects of $\mu$–interferon in renal cell carcinomas: correlation with the expression of a kidney–associated differentiation glycoprotein," Cancer Research 50:4190–4194 (Jul. 15, 1990).

Ogden, B.E., et al.: "Histamine regulates lymphocyte mitogenic responses through activation of specific $H_1$ and $H_2$ histamine receptors. " Immunology 41:107–114 (1980).

Palacios, R., et al.: "Cimetidine abrogates suppressor T cell function in vitro." Immunolgoy Letters 3:33–37 (1981).

Pehamberger, H., et al.: "Effect of BCG on concanavalin A–induced suppressor cell activity and lymphocyte stimulation in stage I melanoma." The Journal of Investigative Dermatology, 76:502–505 (1981).

Radhakrishna Pillai, M., et al.: "Immunocompetence in lung cancer." Cancer 64:1853–1858 (1989).

Rezai, A.R., et al.: "Histamine blocks interleukin 2 (IL–2) gene expression and regulates IL–2 receptor expression." Immunopharmacology and Immunotoxicology 12(3):345–362 (1990).

Richner, J., et al.: "Number of helper T cells and phytohemagglutinin stimulation correlate in cancer patiens." Cancer Immunol. Immunother. 34:138–142(1991).

Roszman, T.L., et al.: "Immunobiology of primary intracranial tumors." Cancer 50:1273–1279 (Oct. 1, 1982).

Rubin, J.T., et al.: "Immunohistochemical correlates of response to recombinant interleukin–2 based immunotherapy in humans." Cancer Research 49:7086–7092 (Dec. 15, 1989).

Silverman, N.A., et al.: "In vitro lymphocyte reactivity and T cells levels in patients with melanoma: correlations with clinical and pathological stage." Surgery, 79(3):332–339 (Mar. 1976).

Sohnle, P.G., et al.: "Differentiation of the effects of preincubation and indomethacin on lymphocyte transformation." Clinical Immunology and Immunopathology 13:47–55 (1979).

Stanojevic–Bakic, N., et al: "T–activin therapy in early stage melanoma patients: in vitro and in vivo immunologic effect." International Journal of Thymology vol. 3, No. 3: 265–272 (1995).

Tilden, A.B., et al.: "Indomethacin enhancement of immunocompetence in melanoma patients." Surgery 90(1):77–84 (Jul. 1981).

Toge, T., et al: "Correlation between lymphocyte responsiveness to mitogens and results of chemo–immunotherapy in patients with advanced cancer." GANN 70:699–703 (Oct. 1979).

Tsubono, M., et al.: "Increased number of suppressor T–cells and impaired IL–2 mediated T–cell function in peripheral blood of gastric cancer patients." J. Clin. Lab. Immunol. 33:107–115 (1990).

Vosixa, G., et al.: "Effect of indomethacin on blastogenesis of lymphocytes from cancer patients: differentiation of patient types." Clinical Immunology and Immunopathology 13:30–38 (1979).

Wang, S.R., et al.: "Histamine suppression of human lymphocyte responses to mitogens." Cellular Immunology 36:28–36 (1978).

Watkins, S.M., et al.: "Cancer prognosis predicted by preoperative lymphocyte responsiveness in vitro." Br. J. Surg. 63:433–434 (1976).

Wilhide, C. C., et al: "An assay for monitoring response to therapy in cancer patients." Annals of Clinical and Laboratory Science. vol. 23, No. 3: 207–215 (1993).

Zighelboim, J., et al.: "Response of normal subjects to mitogens." Clinical Immunology and Immunopathology 19:406–415 (1981).

MONITORING IMMUNOTHERAPY OF MALIGNANT TUMORS

The present invention relates generally to a method of predicting the therapeutic response of a drug. More specifically, the invention relates to a method of predicting the therapeutic response of a drug directed towards a cancer in a human patient.

The response rate for immunomodulating drugs in the treatment of tumours is very low. The most efficient immunomodulating drugs, e.g. interferon or interleukin-2, in the treatment of the most responsive tumours (malignant melanoma and renal cell carcinoma) is only 15–20%. However, some patients achieve very valuable remissions. It would therefore be a considerable improvement if those patients who are most likely to respond to the of treatment could be identified. Several approaches have been used to try to develop such tests. Most of them are based on identification of immunosuppression or activation of certain cells of the immune system in patients with malignant tumours.

Immunosuppression in cancer patients have been demonstrated using various methods, e.g. reduced proliferative stimulation of PBL by mitogens (phytohemagglutinin, PHA and concanavalin A, ConA) or recall antigens (Candida, PPD etc.), reduced response to various antigens on vaccination. In some studies a correlation between the results of these tests and the prognosis of the patients have been reported (e.g. deGast et al., Cancer, 1975; Hilal et al., Am J Surg, 1977).

It has been repeatedly demonstrated that PBL from cancer patients have a significantly lower proliferative response (measured as incorporation of $^3$H-TdR into newly synthesized DNA) to mitogens such as Phytohemagglutinin (PHA) and Concanavallin A (ConA) as compared to normal healthy controls (e.g. Catalona et al., J natl Cancer inst, 1980; Dean et al., Int J Cancer, 1977; Farinas et al., Cancer, 1991; Jerrels et al., Int J Cancer, 1978; Mantovani et al., Diagnostic and Clinical Immunology, 1987; Pehamberger and Knapp, J Invest Dermatol, 1981; Radhakrishna et al., Cancer, 1989; Richner et al., Cancer Immunol Immunother, 1991; Silverman et al., Surgery 1976; Tsubono et al., 1990). Generally, an immunosuppression identified by this technique increases with the advancement of the disease (Lui et al., Br J Cancer, 1975; Mantovani et al., Diagnostic and Clinical Immunology, 1987; Silverman et al., Surgery 1976). Thus, several reports on a correlation between inhibition of the proliferative response and the prognosis of the patients is not surprising. However, they have generally not been found to be useful in the clinical management of individual patients since this immunosuppression is stage dependent and large inter-individual variations are observed in these tests within the group of patients as well as within healthy controls (deGast et al., Cancer, 1975; Lui et al., Br J Cancer, 1975; Silverman et al., Surgery 1976).

Chretien et al. (Chretien et al., Surgery, Gynecology and Obstetrics, 1973) found a reduced proliferative response to PHA before surgery in solid tumour patients compared to normal, age matched controls. In the group of cured patients at the three year follow up, the percentage of patients with a low level of lymphocyte reactivity was significantly lower compared with the group of patients with inoperable or recurrent disease. Similarly, in two other studies the response to PHA was found to correlate with the prognosis (Mekori et al., J Natl Cancer Inst, 1974; Watkins, Br J surg, 1976). In contrast, Hilal et al. (Hilal et al., Am J Surg, 1977) found no correlation between mitogen stimulation and recurrence of squamos cell carcinoma of the head and neck.

These tests have with a few exceptions not been used to predict therapeutic response to chemotherapy (Cheema and Hersh, Cancer, 1971; Jones et al., Clinical Oncology, 1980; Toge et al., Gann, 1979; Wilhide and Larcom, Annals Clin Lab Science, 1993) or immunotherapy. In an attempt to improve this type of tests, some sources of variation were identified and analysed, a procedure which resulted in a proliferative response to PHA which correlated with the effect of chemotherapy (Wilhide and Larcom, Annals Clin Lab Science, 1993). However, this correlation was found only after 2 months of treatment. Thus, there is no predictive value in this test as the response to chemotherapy generally is evaluated after 3 months using radiological investigations of the involved metastatic sites. Cheema and Hersh (Cancer, 1971) found the proliferative response to PHA and streptolysin "O" to be suppressed after chemotherapy. Recovery with a significant overshoot compared to pre-treatment values 8–10 days after chemotherapy correlated with tumour regression. In patients with progressive disease the proliferative response remained suppressed. The lymphocyte responsiveness to PHA has been claimed to predict the response to chemo-immunotherapy (Toge et al., Gann, 1979). However, in this study, unusual response criteria were used and there seems to be a considerble overlapping between the responding and not responding patients, thus making monitoring of individual patients difficult. On the contrary, no effect of chemotherapy on the response to PHA could be demonstrated and a clinically useful difference between responders and non-responders was not found by others (Jones et al., Clinical Oncology, 1980).

The difficulty to identify immunosuppression on an individual base in cancer patients by means of mitogen stimulation of PBL is as pointed out above to a large extent due to the great inter-individual variation in these tests. This source of variation as well as those sources described by Wilhide and Larcom (Wilhide and Larcom, Annals Clin Lab Science, 1993) can be avoided by adding drugs or cytokines with the ability of modulating the immunosuppressor activity to the in vitro cultures of PBL. With this procedure the immunosuppressor activity can be identified within the same set up of cultures by using the same preparation of PBL and the same culture medium. Thus, a comparison with the proliferative rate in cultures of PBL from other individuals at other test occasions is avoided. Furthermore, by using comparisons within the same test occasion the effect of autologous serum in the culture medium on the proliferative response and immunosuppressor activity can be analysed. This is of course highly appropriate as serum factors might play a significant role in immunosuppression. In addition, the inappropriate influence of cytokines in pooled human AB serum or fetal calf serum is avoided.

In the study forming the basis for the present patent application immunomodulating drugs (indomethacin, cimetidine and chlorambucile) were added to mitogen (PHA or ConA) stimulated cultures of PBL from patients with renal cell carcinoma. Indomethacin inhibits cyclo-oxygenase and thereby the synthesis of $PGE_2$, a substance with several down-regulating effects in the immune system. It is well-known within the art that histamine dependent lymphocytes and lymphocytes particularly sensitive to alkylating agents can have an immunosuppressor activity. The possible occurrence of such suppressor activity in cultures of PBL from tumour patients was therefore analysed by adding an alkylating agent, chlorambucil, or cimetidine—a histamine $H_2$ receptor antagonist—to the culture medium. Alkylating agents, particularly cyclophosphamide has been used to down-regulate immunosuppressor activity (see below). As the alkylating activity of this drug requires activtion in vivo, mainly in the liver, another alkylating agent, chlorambucil, was used in the PBL cultures in this study.

Immunosuppressor activity in PBL cultures sensitive to indomethacin, alkylating agents or histamine $H_2$ receptor blockers might identify an immune status which correlates with the response to certain types of immunotherapy. Furthermore, identification of patients with such an immunosuppressor activity might give an opportunity to improve the therapeutic efficacy of immunotherapy since cells with suppressor activity can be eradicated or inhibited by treatment with these immunomodulating drugs.

The effect of addition of indomethacin to mitogen or IL-2 stimulated cultures have been reported in a large number of studies. This drug inhibits cyclo-oxygenase and thereby the synthesis of $PGE_2$, a substance with several down-regulating effects on the immune system. Generally, the proliferative response to mitogens was found to be enhanced by the addition of indomethacin to PBL cultures (Kurosu et al, Jap J surgery, 1988; McCormick and Panje, Cancer Immunol Immunother, 1986; Richner et al., Cancer Immunol Immunother, 1991; Roszman et al., Cancer, 1982; Sohnle and Collins-Lech, Clin Immunol Immunopath, 1979; Tilden and Balch, Surgery, 1981; Vosixa and Thies, Clin Immunol Immunopath, 1979) as well as enhanced or suppressed depending on the concentration the drug (Zieghelboim et al., Clin Immunol Immunopath, 1981). The enhancement was reduced after curative resection and was significantly higher in patients with widespread disease compared with those with localised disease (Kurosu et al, Jap J surgery, 1988) or in patients compared with normal controls (McCormick and Panje, Cancer Immunol Immunother, 1986; Tilden and Balch, Surgery, 1981). Only a few studies have tried to correlate the enhancing effect with the overall prognosis of the patients (Huang et al., Cancer. 1987). A tendency towards an increase of PHA stimulation by the addition of indomethacin was found when head and neck cancer patients with and without recurrencies within four years were compared (Huang et al., Cancer. 1987). Similarly, Braun et al. (Braun et al., Cancer Immunol Immunother, 1983) found the development of indomethacin sensitive (increased PHA stimulation by addition of indomethacin) and glass adherent suppressor cells to preceed disease recurrence.

Histamine can be immunosuppressive or induce immunosuppressor activity. When added to PHA or ConA stimulated cultures of BBL from healthy persons histamine suppressed the proliferative response (Meretey et al., Agents and Actions, 1981; Ogden et al., Immunology, 1980; Rezai et al., Immunopharmacology and Immunotoxicology, 1990; Wang and Zeiman, Cellular Imunology, 1978). This suppressive effect was blocked by the addition of a $H_2$ (Gifford et al., Transplantation, 1980; Meretey et al., Agents and Actions, 1981; Ogden et al., Immunology, 1980; Palacios, Immunol Lett, 1981; Rezai et al., Immunopharmacology and Immunotoxicology, 1990; Wang and Zeiman, Cellular Imunology, 1978) but not a $H_1$ receptor antagonist (Ogden et al., Immunology, 1980; Rezai et al., Immunopharmacology and Immunotoxicology, 1990; Wang and Zeiman, Cellular Imunology, 1978). The effect of $H_1$ and $H_2$ receptor stimulation seems to be dose dependent (Beaulieu et al., Int Arch Allergy appl Immun, 1986). There are no reports on any predicitve value of these tests.

It is well-known within the art that immunosuppressor activity can be down-regulated by in vivo administration of alkylating agents, e.g. cyclophoshamide (Berd et al., Cancer Research, 1984; Hoon et al., Cancer Research, 1990; Livingstone et al., J Biol Response Modifiers, 1987). There have been no reports on the effects of alkylating agents on the proliferative response of PBL to mitogens or IL-2 in vitro.

In an experimental model in the mouse the expression of a glycoprotein (gp 160) in renal cell carcinoma cell lines was found to correlate with resistance to interferon-α (Nanus et al., Cancer Research, 1990).

In patients with metastatic colorectal carcinoma the serum level of C-reactive protein (CRP) was found to correlate with the therapeutic response to continous infusion of interleukin-2. Patients with a low initial level and a significant increase in serum level of CRP during treatment did respond significantly better than those with a high initial level with no increase in serum level during therapy (Broom et al., Br J Cancer, 1992).

Activation of subsets of lymphocytes, demonstrated as an increased number of HLA-Dr+ cells in the peripheral blood before the initiation of interleukin-2 treatment, was found to discriminate between responders and non-responders (Janssen et al., Br J Cancer, 1992). The density of a natural killer cell-associated antigen (CD56) on NK-cells in the peripheral blood was found to differ significantly between renal cell carcinoma patients responding and not responding to treatment with interleukin-2 in combination with interferon-α. A difference between patients with a stable disease and a tumour regression was, however, only found after six weeks of treatment (Duensing et al., Mol Biother, 1992).

Regressing lesions after interleukin-2 based therapy were found to be permeated by CD4 and CD8 T-cells as well as macrophages. DR-antigen was expressed in seven out of seven regressing metastases compared to only three out of ten of non-regressing lesions (Rubin et al., Cancer Research, 1989). The serum concentration of the tumour necrosis factor-α after infusion of interleukin-2 in combination with lymphokine-activated killer cells was 48 hours after the termination of the treatment claimed to be higher in responders as compared with non-responders. However, there seems to be an overlapping between those groups which reduce the predictive value of this analysis when individual patients are monitored (Blay et al., Cancer Research, 1990). The results of these two studies can hardly be used to predict the outcome of immunotherapy as they appear only after treatment.

It has thus been known for a long time that an immunosuppression exists in patients having a tumour. This suppression can for example be demonstrated as an impaired proliferative response of blood lymphocytes after stimulation with mitogens such as PHA and ConA. In spite of the fact that the basic data have been known for several decades nobody has developed or described a method based on such data, the method having a predictive value in immunotherapy. One reasons for this is probably that upon mitogen stimulation of blood lymphocytes the range of variation is considerable within the control as well as within the patient group. Methods based on such comparisons are thus not useful for monitoring individual patients. By adding immunomodulating drugs to mitogen stimulated cultures comparisons can be performed with data which are obtained from a culture originating from one and the same patient, a procedure which considerably reduces the variance in a sample.

By using the correct immunomodulating drug it is possible to differentiate between patients who respond and do not, respectively, respond to immmunotherapy. This principle has been shown to work for two quite different immunomodulating drugs, interferon-α and interleukin-2. Furthermore, two types of immunosuppression have been shown to exist with patients responding to these drugs. It is thus most probable that the principle described also will work with other types of immunotherapy.

Accordingly, it is a purpose of the present invention to produce a method of predicting the therapeutic response of a drug directed towards a cancer in a human patient, using samples of immunocompetent cells taken from said patient at different times.

In order to achieve this purpose, the method according to the invention has been given the characterizing feature of claim 1.

By analysing the proliferative response to mitogens or IL-2, alone or in combination with immunomodulating drugs, several differences are demonstrated between patients with a stable, progressive disease or a tumour regression. Particularly, the effect of chlorambucil on PHA stimulated cultures seem to be of value in identification of patients with a high probability to respond to IL-2 treatment. Similarly, the enhancement of PHA stimulation by cimetidine identifies responders to IFN-a treatment. It is also possible by means of the method according to the invention to predict and monitor immunotherapy.

In order to further explain the invention reference is made to the accompanying drawings.

MATERIAL AND METHODS

Patient data.

This study includes 23 evaluable patients with renal cell carcinoma (RCC) treated with IL-2 and 19 evaluable patients treated with IFN-a. All tumours were histologically or cytologically proven. In the group of IL-2 treated patients, fourteen had only one metastatic site, four had two sites and five had three or more sites. In the group of IFN-a treated patients, four had only one metastatic site, eight had two sites and seven had three or more sites. No patient had been treated previously except for surgical removal of primary tumour or metastases.

Patient evaluation.

Pre-treatment investigations included electrocardiogram (ECG), abdominal computerized tomography/ultra sound (CT/US), chest X-ray, bone scintigraphy and blood samples for measurements of creatinine, bilirubin, alkaline phosphatase, aspartate-aminotranferase, alanine-aminotrasferase, lactate-dehydrogenase, alpha amylase, haemoglobin, white blood cells and thrombocytes. The immune function parameters (see below) were analysed during the first three treatment weeks. The patients were re-evaluated for tumour response after three treatment cycles. Responding patients were subjected to continued treatment with regular evaluation.

Treatment procedure.

Interferon-a-2b: Interferon-a-2b (IFN-a, Schering Plough, Sweden) was given s.c. three days weekly at a dose of 10 milj.IU. In addition patients 17 were also treated with cyclophosphamide at a dose of 300 mg/m$^2$ administered as i.v. bolus every three weeks and 12 of these patients were also treated with 50 mg of Indomethacin three times daily. Three patients were on cimetidine medication.

Interleukin-2: Patients received subcutaneous (sc) Interleukin-2 (IL-2, EuroCetus/Farmos, Sweden) at $4.8 \times 10^6$ IU/m$^2$ ($=0.8 \times 10^6$ CU/m$^2$) per single dose given every 12 hours on days 1 through 5 every other week. The duration of one treatment cycle was two weeks. Chlorambucil at a dose of 5 mg daily for 5 days was added to the IL-2 treatment starting on day 3 in cycle two. During the first week of IL-2 treatment the patients were in the hospital in order to find out a reasonable dose-level allowing the patient to continue treatment with tolerable side-effects on an outpatient basis. Almost all patients needed dose-adjustments, the delivered dose in most cases being between 50–75% of the calculated dose Criteria of response (accrding to WHO) and related defenitions.

Complete response (CR): Disappearance of all known disease. Partial response (PR): Decrease by at least 50% in the sum of the products of the largest perpendicular diameters of measurable lesions determined by two observations not less than 4 weeks apart. It is not necessary for all lesions to have regressed to qualify for partial response but no lesion should have progressed and no new lesions should appear. Minor regressions did not fullfill the criteria for partial regression, either because the reduction in the tumour size was 25% to 50% or the duration of the response was to short.

Mixed response (MR) defined as measurable shrinkage of some lesion and simultaneous signs of a progressive disease in some other metastasis or appearance of new lesions. Stable disease (SD): A 25% decrease in total tumor size cannot be established nor has a 25% increase in the size of one or more measurable lesions been demonstrated. In addition, there is no appearance of new lesions. Progressive disease (PD): A 25% or more increase in the size of at least one measurable lesion or the appearance of a new lesion. Time to progression, survival: From the first day of treatment to the date of first observation of a progressive disease in all eligible patients. Survival: From the first day of treatment to the date of death in all eligible patients.

Cell cultures.

Heparinized blood samples were collected between 8–10 a. m., and all samples were processed within 1 hr after the blood had been taken. Mononuclear cells were isolated by Ficoll-Isopaque (Pharmacia, Uppsala, Sweden) density gradient centrifugation. One hundred $\mu$l of PBMC in culture medium at a concentration of $0.6\times10^6$ cells/ml were seeded into round-bottomed microtiter plates (Corning, N.Y., USA) together with 100 $\mu$l of culture medium consisting of RPMI 1640 (Flow Laboratories, Irvine, Scotland), supplemented with inactivated (56° C. for 30 min.) AB serum (control cultures) or autologous fresh serum (patient cultures) at a final concentration of 10%. The culture medium also contained a combination of Penicillin 5000 IU/ml and Streptomycin 5000 $\mu$g/ml (PEST) Flow Laboratories, Irvine, Scotland), final concentration 2%.

Ten $\mu$l of concanavalin A (ConA, Sigma Chemical, St. Louis, Mo., USA, 400 $\mu$g/ml, final concentration 40 $\mu$g/ml)) or phytohemagglutinin (PHA, Sigma Chemical, St. Louis, Mo., USA, 200 $\mu$g/ml, final concentration 20 $\mu$g/ml) or IL-2 (1200 IU/ml, final concentration 120 IU/ml) were added for mitogenic stimulation. Cells were cultured for 2 days in a humidified 5% $CO_2$ atmosphere at 37° C. Proliferation was assayed by incorporation of 20 $\mu$l/well of $^3$H-thymidine (80 $\mu$Ci/ml, 1.6 $\mu$Ci/well; Amersham International, United Kingdom) for 18 hr at 37° C. Mean values of dpm (disintegrations per minute) of triplicates were used for the calculations.

Influence of immunomodulating (pharmacological) agents on cell stimulation.

Ten $\mu$l of the following pharmacological agents were added to the mitogen stimulated cultures: Indomethacin (Sigma Chemical), chlorambucil (Sigma Chemical) or cimetidine (Tagamet®, Smith, Kline & French, Travenol, Halden, Norway); all at a concentration of 20 $\mu$g/ml, final concentration 1 $\mu$g/ml.

Statistical analysis.

Comparisons between the proliferative response to mitogens (ConA or PHA) or IL-2 in different groups or at different test occasions were performed on mean values of dpm from triplicate samples by means of an unpaired t-test. For the determination of the effect of addition of immunomodualting drugs a modulation index was calculated as follows:

MODULATION INDEX=log $dpm$ (ConA,PHA or IL-2)+drug/$dpm$ (ConA,PHA or IL-2)

Comparisons of the means of modulation index for different patient groups or different test occasions were performed by means of an unpaired t-test.

The purpose of the present invention was to obtain a possible correlation between the capacity of RCC patients to respond to immunotherapy (e.g. IL-2 or IFN-a treatment), measured as regression of metastases, and systemic immunosuppression, measured as proliferative response of PBL to mitogenes or cytokines (e.g. IL-2) alone or in combination with the immunomodulating drugs (e.g. indomethacin, chlorambucil or cimetidine). Therefore, it was considered most appropriate to include all patients with significant tumour regressions, that is also minor regressions and mixed responses as responding patients in this analysis.

EXAMPLE 1

Analysis of IFN-α Treatment

Therapeutic effect of IFN-α

Measurable regression after IFN-α treatment was recorded in five cases, PR (2), RR (2) (minor regressions not fulfilling the criteria for partial remission either because the tumour shrinkage was less than 50% or the duration of the remission was too short), MR (1). Six patients had a stable and eight a progressive disease.

Proliferative response of mitogen stimulated PBL

Figure 1:
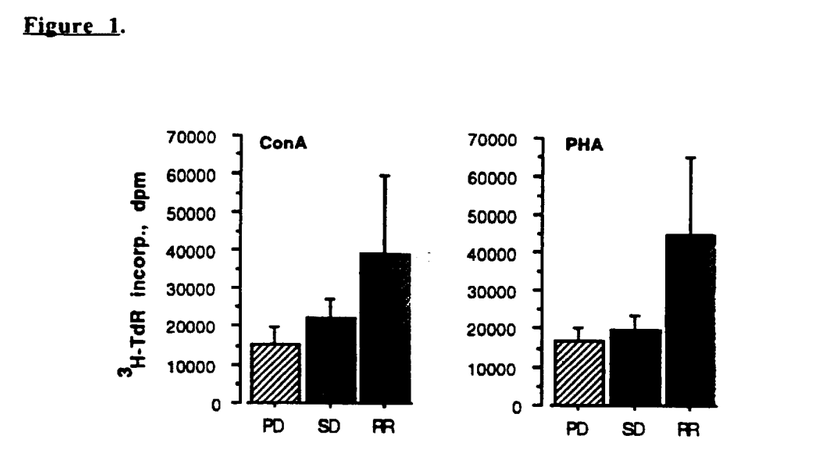
FIG. 1 shows the proliferative response to ConA or PHA of PBL from renal cell carcinoma patients with a progressive disease (PD), a stable disease (SD) and a tumour regression (RR) before initiation of interferon-$\alpha$ treatment.

The proliferative response of PBL to mitogenes (PHA and ConA) alone or in combination with immunomodulating drugs was studied before initiation of IFN-α treatment. As can be seen from FIG. 1, there is a tendency to a difference in proliferative response to ConA and PHA between PBL from patients with a progressive disease and a tumour regression, p=0.19 and p=0.11, respectively. If non-responders (stable and progressive disease) are compared with responders, the proliferative response to PHA differs significantly, p=0.04.

Figure 2:
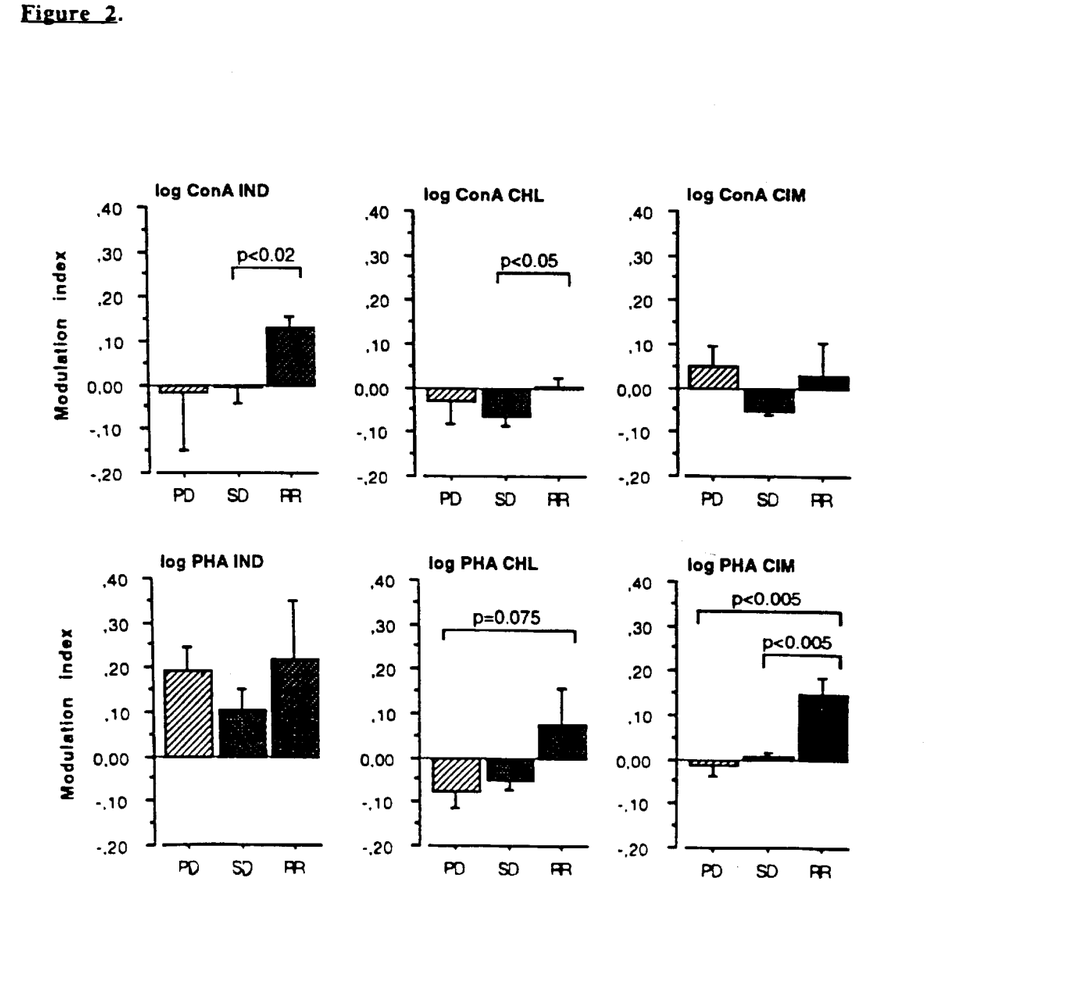
FIG. 2 shows the modulation of the proliferative response of PBL from renal cell carcinoma patients to ConA or PHA by the addition of indomethacin (IND), chlorambucile (CHL) or cimetidine (CIM). The tests were performed before initiatin of INF-$\alpha$ treatment. Comparison of patients with a progressive disease (PD), a stable disease (SD) and a tumour regression (RR).
Figure 3:
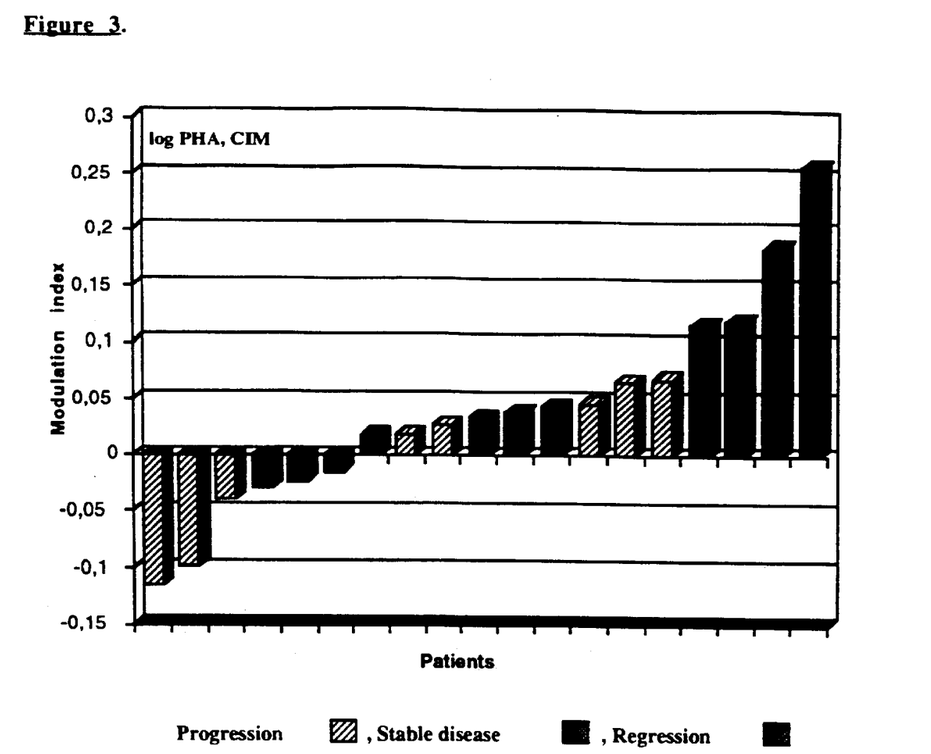
FIG. 3 shows the modulation of the proliferative response to PHA by the addition of cimetidine. The tests were performed before initiation of IFN-$\alpha$ treatment. Each bar represents one patient.

The effect of immunomodulating drugs on the proliferative response to ConA or PHA in relation to response to IFN-α treatment is demonstrated in FIG. 2. ConA stimulation is significantly enhanced by indomethacin in PBL from responders as compared to patients with a stable disease (p<0.02). The proliferative response is suppressed by chlorambucil in non-responders both after ConA and PHA stimulation, with a statistically significant difference between patients with tumour regression and a stable disease after ConA stimulation and a tendency to a significant difference between patients with a progressive disease and a tumour regression after PHA stimulation. Cimetidine does not seem to have any effect on ConA stimulation in these patients. In contrast, the response to PHA by PBL from patients achieving regression on IFN-α treatment, is significantly enhanced as compared to patients with a stable (p<0.005) or a progressive disease (p<0.005). Cimetidine enhancement of the proliferative response to PHA can be used to identify responders to IFN-α treatment. As demonstrated in FIG. 3 four out of five patients achieving tumour regression on this therapy differs markedly from patients with a stable or a progressive disease.

EXAMPLE 2

Analysis of IL-2 Treatment

Therapeutic effect of IL-2

A measurable regression after IL-2 treatment was recorded in 12 cases, CR (2), PR (1), RR (7) (minor regressions not fulfilling the criteria for partial remission either because the tumour shrinkage was less than 50% or the duration of the remission was too short), MR (2). Four patients had a stable and nine a progressive disease. Eight responders and three patients with a stable disease achieved prolonged disease control.

Proliferative response of mitogen or IL-2 stimulated PBL.

The proliferative response of PBL to mitogenes, PHA and ConA, or IL-2 was studied weekly during the first three weeks on treatment.

The response to ConA (FIG. 4) and PHA (FIG. 5) immediately before the start of IL-2 treatment was significantly higher in PBL cultures from patients achieving tumour regression as compared to patients with a progressive disease ($p<0.05$). The proliferative response in PBL cultures from patients with a stable disease did not differ significantly from that in cultures from patients with either a progressive disease or a tumour regression. In IL-2 stimulated cultures (FIG. 6) there was almost no difference between patients with a tumour regression, a stable disease and a tumour progression.

Figure 4:
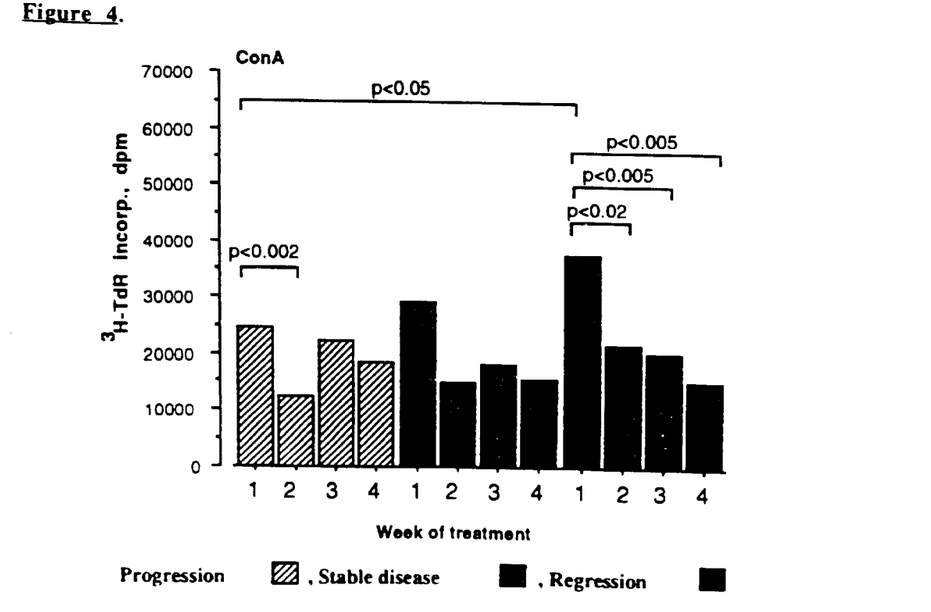
FIG. 4 shows the proliferative response of PBL from renal cell carcinoma patients to ConA before and during IL-2 treatment. The tests were performed as follows: Test one (1) just before the start of the treatment, test two (2) one week later, 48 hours after five days of IL-2 treatment, test three (3) after one week without IL-2 administration, and test four (4) one week later, 48 hours after another five days of IL-2 treatment combined with chlorambucil. The patients were divided into three groups according to the response to therapy, i.e. progression, a stable disease and regression.
Figure 5:
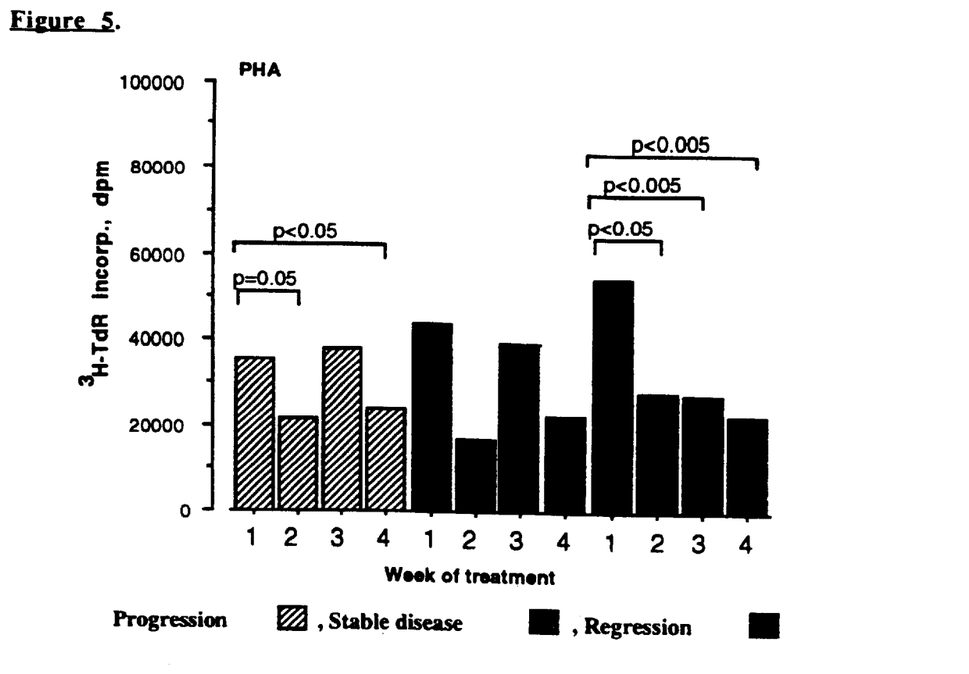
FIG. 5 shows the proliferative response of PBL from renal cell carcinoma patients to PHA before and during IL-2 treatment. The test procedures were as in FIG. 4.
Figure 6:
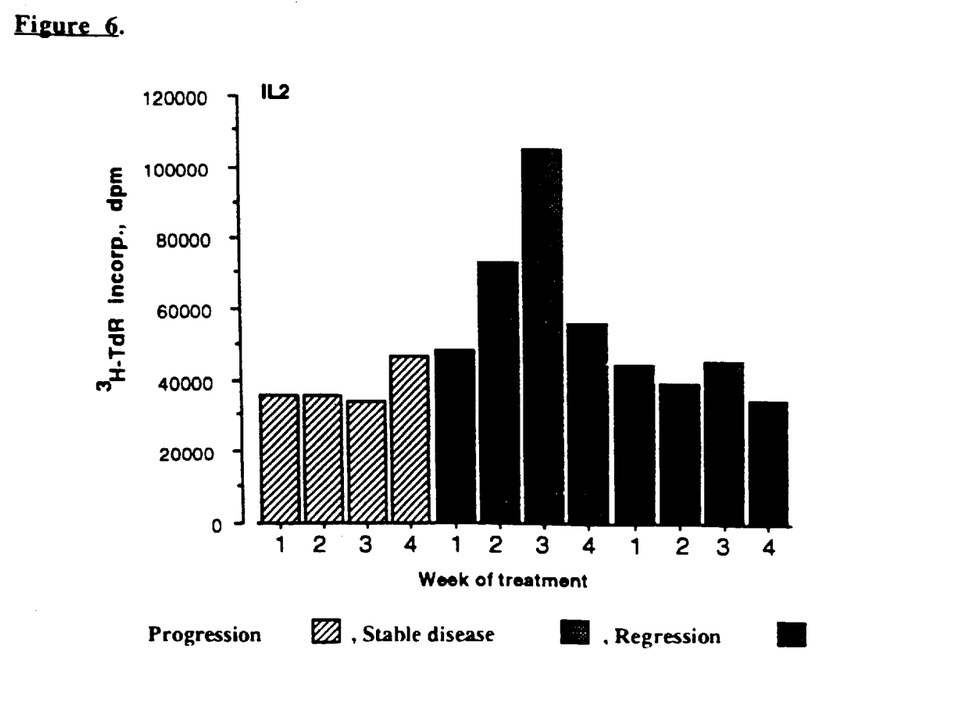
FIG. 6 shows the proliferative response of PBL from renal cell carcinoma patients to IL-2 in vitro before and during IL-2 treatment. The test procedures were as in FIG. 4.

After one week on IL-2 therapy, the response to ConA ($p<0.002$) and PHA ($p<0.05$) was significantly reduced in comparison with tests before treatment in patients with a tumour regression and a progressive disease. A similar tendency was also found in patients with a stable disease. However, due to the low number of patients in this group a statistical significance was not attained. In contrast, the proliferative response to IL-2 in vitro was not significantly changed in any patient group, but there was a tendency to an increased stimulation in cultures from patients with a stable disease.

After the second week of the first treatment cycle without IL-2 administration the proliferation induced by ConA and PHA was markedly restituted in patients with a progressive disease and did not differ significantly from that before initiation of the IL-2 treatment. In responders, however, the response to ConA and PHA was not restituted in comparison with tests performed after the first week of treatment and was still significantly reduced in comparison with the responses obtained before the treatment was initiated. The change in proliferative response to ConA and PHA (compared as above) between non-responders and responders at this time was also significantly different, $p<0.05$ and $p<0.001$, respectively. In patients with a stable disease the response to ConA was only slightly restituted in contrast to PHA cultures where the response was similar to that found in cultutres from patients with a progressive disease. There were no significant changes in the response of PBL to IL-2 in vitro in any group of patients.

After another week of IL-2 treatment (now combined with chlorambucil) the proliferative response to ConA and PHA was again reduced in all groups of patients, but these changes were significant only in PHA cultures from patients with a progressive disease ($p<0.05$) and a tumour regression ($p<0.005$). In IL-2 stimulated cultures the proliferative response of PBL was not significantly changed.

In order to further analyse differences between patients with a progressive, stable or regressive disease the immunomodulating drugs indomethacin, chlorambucil or cimetidine were added to mitogen and IL-2 stimulated PBL cultures.

Figure 7:
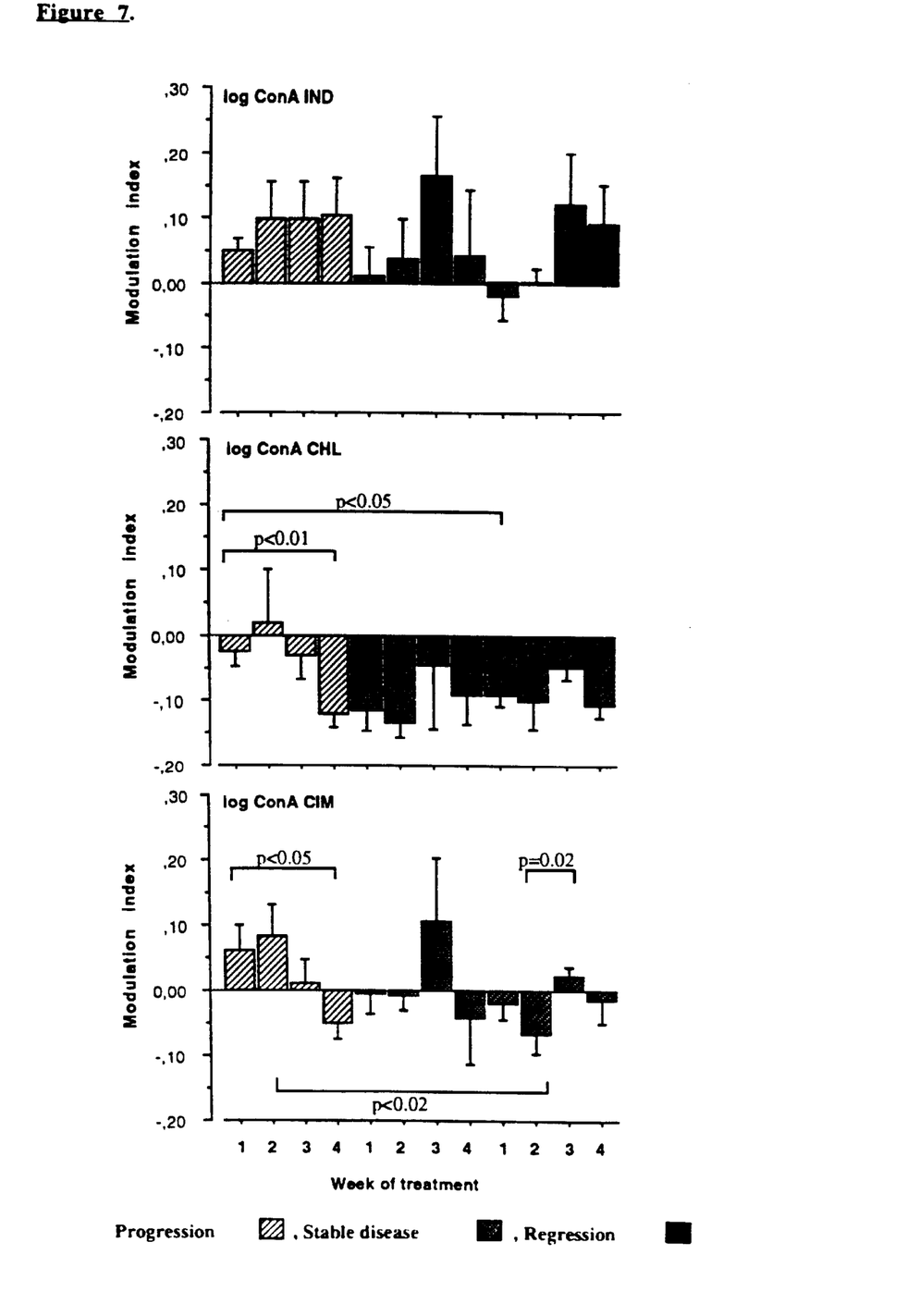
FIG. 7 shows the effect of immunomodulating drugs on the proliferative response of PBL to ConA. The test procedures were as in FIG. 4.

As can be seen from FIG. 7, addition of indomethacin to ConA cultures resulted in a slight increase of the proliferative response, but these changes were not statistically significant. In contrast, indomethacin significantly increased the proliferative response in PHA cultures (FIG. 8) from patients with a progressive disease after the first week of IL-2 treatment. This effect disappeared after one week without IL-2 administration (when the proliferative response to PHA was restituted) but reappeared after administration of IL-2 in the second treatment cycle. A similar effect of indomethacin was found in PBL cultures from patients with a stable disease. In cultures from responders indomethacin significantly enhanced the proliferative response to PHA after one week of treatment only. This effect then gradually decreased during the following weeks.

There was a significant difference in the effect of indomethacin on IL-2 stimulated PBL cultures (FIG. 9) from patients with a stable disease and those with a tumour regression ($p<0.005$). The proliferative response was stimulated in the former group and inhibited in PBL from the responders. A tendency to a similar difference was also found between non-responders and responders ($p=0.067$).

Figure 8:
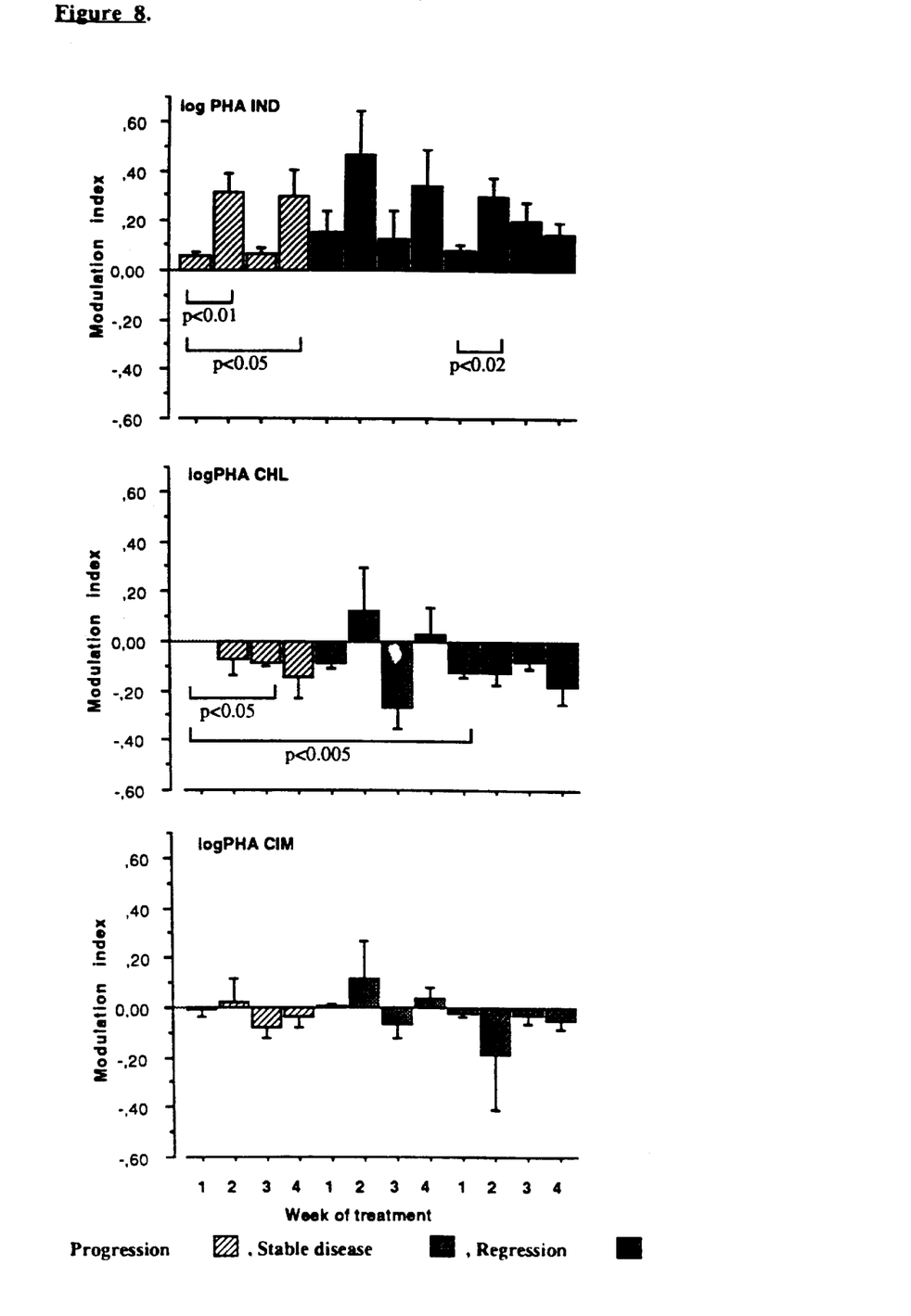
FIG. 8 shows the effect of immunomodulating drugs on the proliferative response of PBL to PHA. The test procedures were as in FIG. 4.
Figure 9:
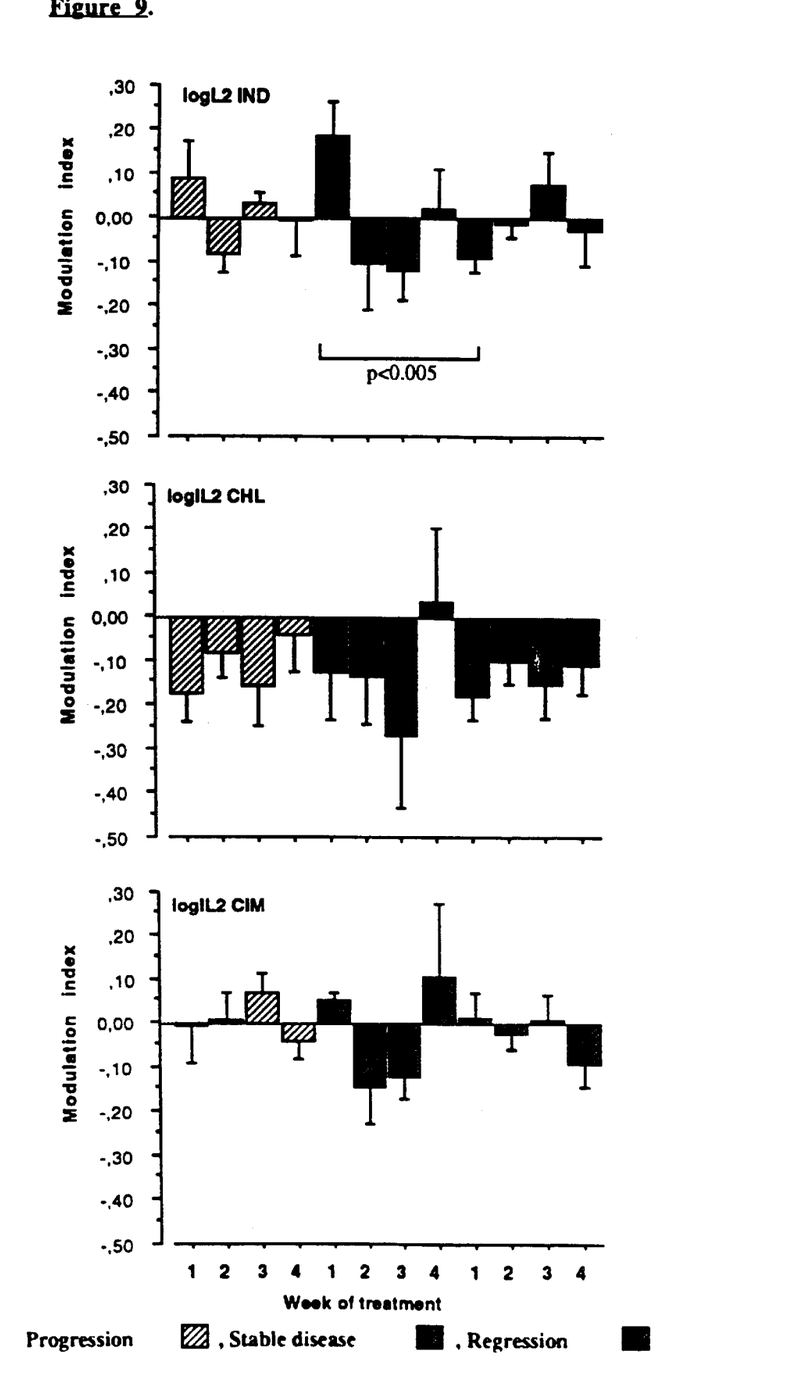
FIG. 9 shows the effect of immunomodulating drugs on the proliferative response of PBL to IL-2 in vitro. The test procedures were as in FIG. 4.
Figure 10:
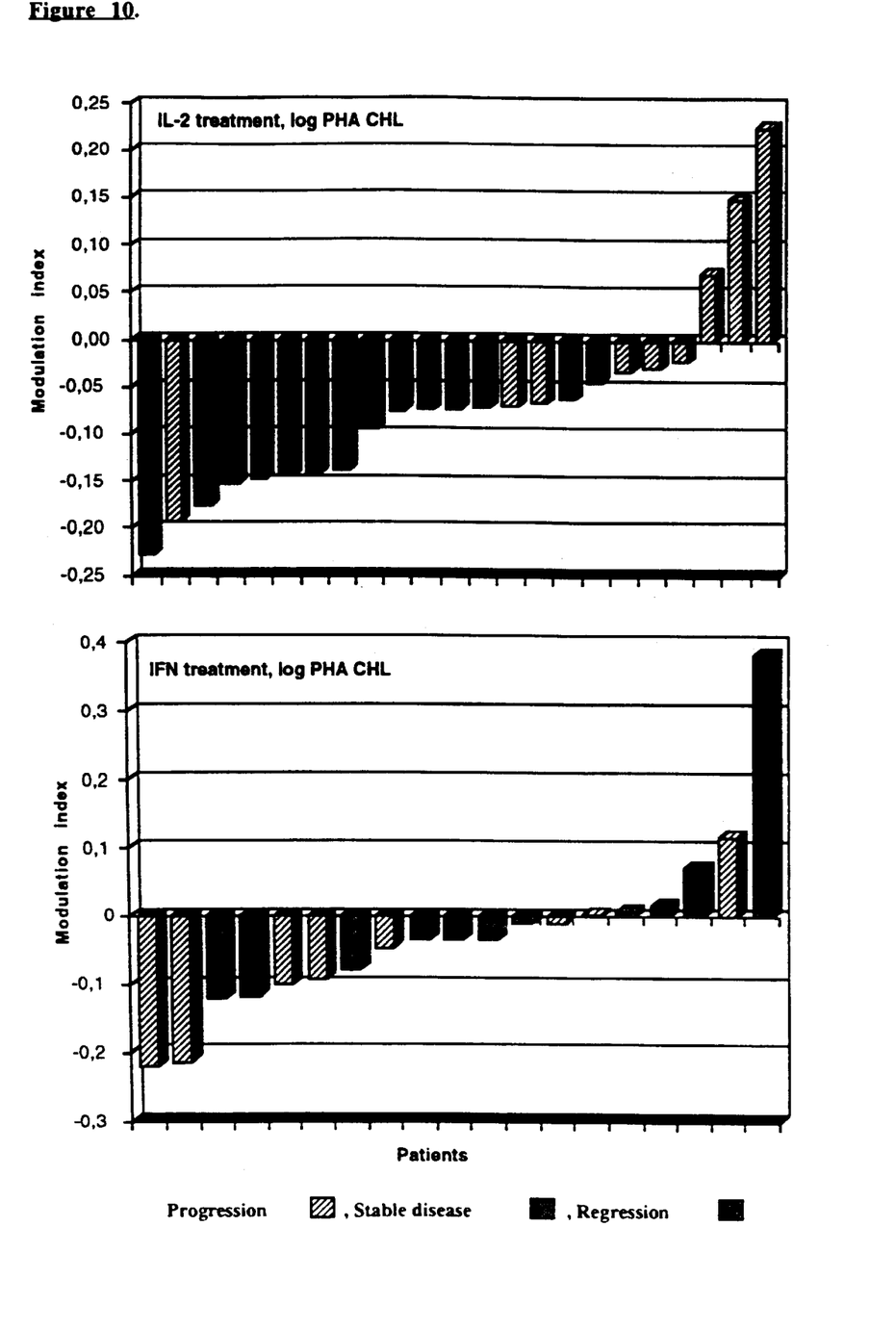
FIG. 10 shows the comparison of the effect of chlorambucil on PHA stimulation of PBL from patients treated with IL-2 or IFN-$\alpha$. Each bar represents one patient.

Chlorambucil had no effect on the response to ConA (FIG. 7) or PHA (FIG. 8) in cultures obtained before the initiation of IL-2 treatment in patients with a progressive disease. In contrast, in patients with a tumour regression the proliferative response was significantly inhibited in ConA ($p<0.05$) as well as PHA stimulated cultures ($p<0.005$). A significant inhibition of the proliferative response to these two mitogens appeared, however, during the treatment period in patients with a progressive disease. There were no significant differences between non-responders and responders in IL-2 stimulated cultures in the presence of chlorambucil (FIG. 9). As shown in FIG. 10, patients with a proliferative response to PHA being markedly suppressed by chlorambucil are far more likely to achieve a tumour regression than those who have only a slight suppression or have an enhancement of the response by chlorambucil.

Cimetidine significantly modulated the response to ConA (FIG. 7) at several occasions during the treatment period with IL-2, but there were no significant differences between patients with a stable, progressive disease or a tumour regression in cultures set up before initiation of therapy.

EXAMPLE 3

Comparison between responders to IL-2 and IFN-a treatment.

Figure 11:
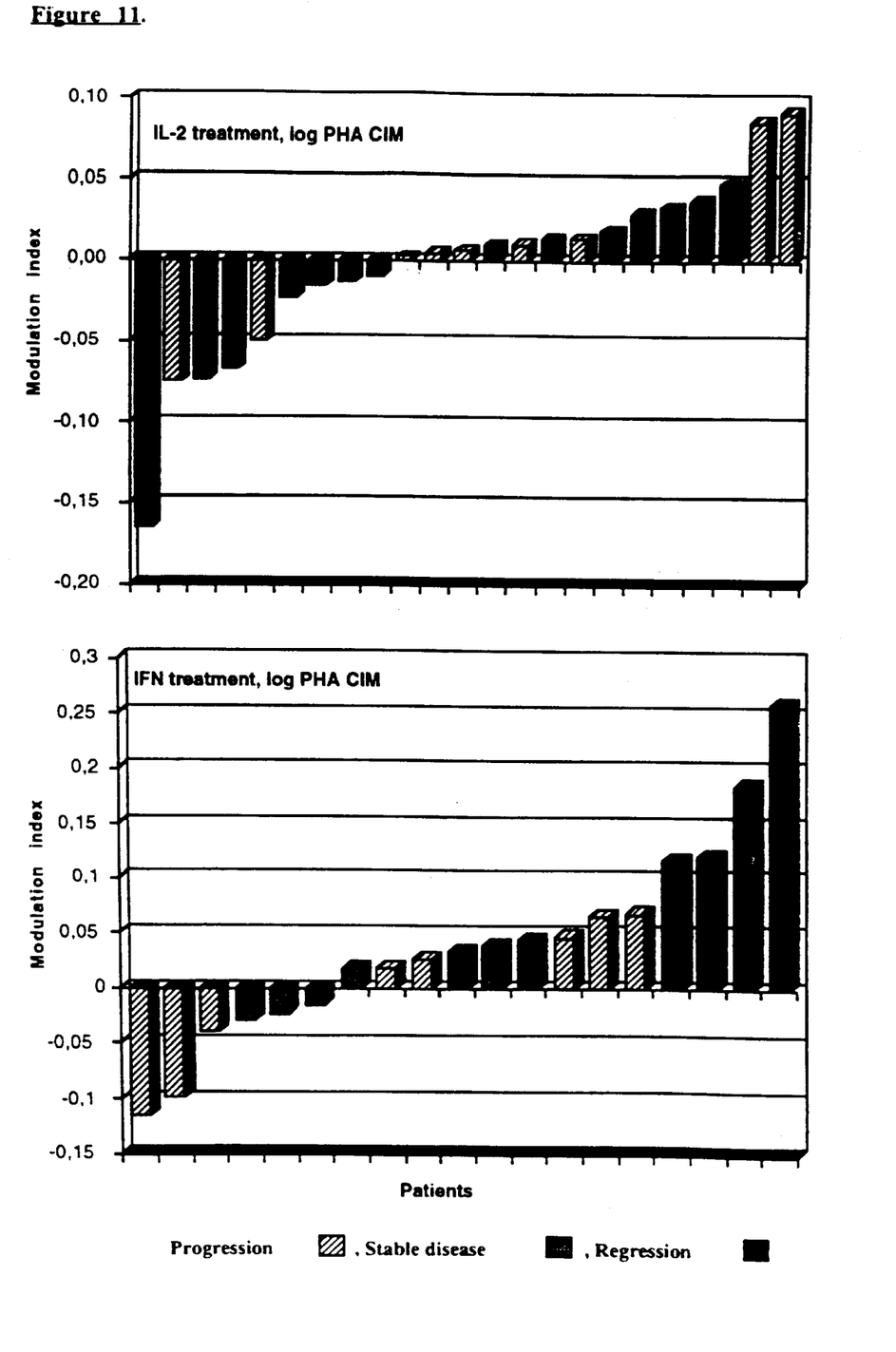
FIG. 11 shows the comparison of the effect of cimetidine on PHA stimulation of PBL from patients treated with IL-2 or IFN-$\alpha$. Each bar represents one patient.

The relationship between the therapeutic effect and the modulating effect of chlorambucil on the proliferative response of PBL to PHA before initiation of IL-2 or IFN-a was compared. As demonstrated in FIG. 2 chlorambucil enhanced the proliferative response of PBL from patients, who achieve a tumour regression on IFN-a treatment, but reduced the response of PBL from patients with a stable disease or a tumour progression. In contrast, the response of PBL, from responders to IL-2 treatment, to PHA was significanly inhibited (FIG. 8). Tests for each patient are shown in FIG. 10. A similar difference is also found in the effect of cimetidine on the response to PHA. PBL from responders to IFN-a were stimulated by addition of this drug to PHA cultures as compared to PBL from non-responders (FIGS. 2 and 8). Cimetidine had no significant effect on the PHA stimulation of PBL from IL-2 responders. Tests for each patient are shown in FIG. 11. Thus, there is a marked difference in the immune status of renal cell carcinoma patients responding to IL-2 or IFN-a.

Thus, a correlation has been obtained between the capacity of renal cell carcinoma patients to respond to Interleukin-2 (IL-2) or Interferon-a (IFN-a) treatment, measured as regression of metastases, and systemic immunosuppression, measured as proliferative response of peripheral blood lymphocytes (PBL) to mitogenes or IL-2 alone or in combination with the immunomodulating drugs, indomethacin, chlorambucil or cimetidine.

References

Beaulieu, L., et al: Effects of $H_1$ and $H_2$ Receptor Agonists on Nonspecific Proliferative Response of Human Peripheral Blood Lymphocytes. Int Archs Allergy appl Immun 79:249–252 (1986).

Berd, D.; Maguire Jr., H. C.; Mastrangelo, M. J.: Impairment of Concanavalin A-inducible Suppressor Acitivity following Administration of Cyclophosphamide to Patients with Advanced Cancer. Cancer Research 44:1275–1280 (1984).

Blay, J. Y., et al: Correlation between Clinical Response to Interleukin 2 Therapy and Sustained Production of Tumor Necrosis Factor. Cancer Research 50:2371–2374 (1990).

Braun, D. P., et al: Serial immune testing in surgically resected lung cancer patients. Cancer immunol immunother 15:114–120 (1983).

Broom, J., et al: Interleukin 2 therapy in cancer: identification of responders. Br J Cancer 66:1185–1187 (1992).

Catalona, W. J.; Ratliff, T. L.; McCool, R. E.: Concanavalin A-Activated Suppressor Cell Activity in Peripheral Blood Lymphocytes of Urologic Cancer Patients. JNCI 65:553–557 (1980).

Cheema, A. R.; Hersh, E. M.: Patient survival after chemotherapy and its relation-ship to in vitro lymphocyte blastogenesis. Cancer 28:851–855 (1971).

Chretien, P. B., et al: Correlation of preoperative lymphocyte reactivity with the clinical course of cancer patients. Surg, Gynecol & Obst 136:380–384 (1973).

Dean, J. H., et al: The relative proliferation index as a more sensitive parameter for evaluating lymphoproliferative responses of cancer patients to mitogens and alloantigens. Int J Cancer 20:359–370 (1977).

Duensing, S., et al: Pretreatment natural killer antigen density correlates to clinical response in tumor patients receiving long-term subcutaneous recombinant interleukin-2 and recombinant interferon-a. Mol Biother 4:170–173 (1992).

Fariñas, M. C., et al: Contribution of Monocytes to the Decreased Lympho-proliferative Response to Phytohemagglutinin in Patients With Lung Cancer. Cancer 68:1279–1284 (1991).

de Gast, G. C., et al: Humoral and cell-mediated immune response in patients with malignant melanoma. I. In Vitro Lymphocyte Reactivity to PHA and Antigens Following Immunization. Cancer 36:1289–1297 (1975).

Gifford Sr, R. R.; Hatfield, S. M.; Schmidtke, J. R.: Cimetidine-induced augmentation of human lymphocyte blastogenesis by mitogen, bacterial antigen, and alloantigen. Transplantation 29:143–148 (1980).

Hilal, E. Y., et al: Immunologic Evaluation and Prognosis in Patients with Head and Neck Cancer. Am J Surg 134:469–473 (1977).

Hoon, D. S. B., et al: Suppressor Cell Activity in a Randomized Trial of Patients Receiving Active Specific Immunotherapy with Melanoma Cell Vaccine and Low Dosages of Cyclophosphamide. Cancer Research 50:5358–5364 (1990).

Huang, A. T., et al: A Prospective Study of Squamous Head and Neck Carcinoma. Immunologic Aberrations in Patients Who Develop Recurrent Disease. Cancer 59:1721–1726 (1987).

Janssen, R. A. J, et al: Peripheral blood lymphocyte number and phenotype prior to therapy correlate with response in subcutaneously applied rIL-2 therapy of renal cell carcinoma. Br J Cancer 66:1177–1179 (1992).

Jerrells, T. R.; Dean, J. H.; Herberman, R. B.: Relationship between T lymphocyte levels and lymphoproliferative responses to mitogens and alloantigens in lung and breast cancer patients. Int J Cancer 21:282–290 (1978).

Jones, K. D., et al: Lymphocyte response to PHA and patient response to chemo-therapy in breast cancer. Clin Oncol 6:159–166 (1980).

Kurosu, Y.; Arai, T.; Morita, K.: Indomethacin Enhancement of Lymphocyte Responses to Phytohemagglutinin in Breast, Stomach and Colorectal Cancer Patients. Japanese J Surg 18:152–157 (1988).

Livingston, Ph. O., et al: Inhibition of Suppressor-Cell Acitivity by Cyclo-phosphamide in Patients with Malignant Melanoma. J Bio Resp Mod 6:392–403 (1987).

Lui, V. K., et al: Cellular immunocompetence in melanoma: Effect of extent of disease and immunotherapy. Br J Cancer 32:323–330 (1975).

Mantovani, G., et al: Interleukin 2 (IL 2) Relationships With the Cancer-Related Immunodeficiency: In Vitro Response to Exogenous IL 2 by PHA-Activated and Non PHA-Activated Peripheral Blood Mononuclear Cells From Cancer Patients. Diagn Clin Immunol 5:104–111 (1987).

McCormick, K. J.; Panje, W. R.: Indomethacin-induced augmentation of lympho-proliferative responses in patients with head and neck cancer. Cancer Immunol Immunother 21:226–232 (1986).

Mekori, T.; Shulamith, S.; Robinson, E.: Suppression of the mitogenic response to phytohemagglutinin in malignant neoplasia: Correlation with clinical stage and therapy. J Natl Cancer Inst 52:9–12 (1974).

Meretey, K.; Room, G.; Maini, R. N.: Effect of histamine on the mitogenic response of human lymphocytes and its modification by cimetidine and levamisole. Agents and Actions 11:84–88 (1981).

Nanus, D. M., et al: Antiproliferative and Antitumor Effects of a-Interferon in Renal Cell Carcinomas: Correlation with the Expression of a Kidney-associated Differentiation Glycoprotein. Cancer Research 50:4190–4194 (1990).

Ogden, B. E.; Hill, H. R.: Histamine regulates lymphocyte mitogenic responses through activation of specific $H_1$ and $H_2$ histamine receptors. Immunol 41:107–114 (1980).

Palacios, R.; Alarcon-Segovia, D.: Cimetidine abrogates suppressor T cell function in vitro. Immunol Lett 3:33–37 (1981).

Pehamberger, H.; Knapp, W.: Effect of BCG on Concanavalin A-induced Suppressor Cell Activity and Lymphocyte Stimulation in Stage I Melanoma. J Invest Dermatol 76:502–505 (1981).

Radhakrishna Pillai, M., et al: Immunocompetence in Lung Cancer. Relationship to Extent of Tumor Burden and Histologic Type. Cancer 64:1853–1858 (1989).

Rezai, A. R., et al: Histamine blocks Interleukin 2 (IL-2) gene expression and regulates IL-2 receptor expression. Immunopharm Immunotox 12:345–362 (1990).

Richner, J., et al: Number of helper T cells and phytohemagglutinin stimulation correlate in cancer patients. Cancer Immunol Immunother 34:138–142 (1991).

Roszman, T. L.; Brooks, W. H.; Elliott, L. H.: Immunobiology of Primary Intracranial Tumors. VI. Suppressor Cell Function and Lectin-binding Lymphocyte Subpopulations in Patients with Cerebral Tumors. Cancer 50:1273–1279 (1982).

Rubin, J. T., et al: Immunohistochemical Correlates of Response to Recombinant Interleukin-2-based Immunotherapy in Humans. Cancer Research 49:7086–7092 (1989).

Silverman, N. A., et al: In vitro lymphocyte reactivity and T cell levels in patients with melanoma: Correlations with clinical and pathological stage. Surgery 79:332–339 (1976).

Sohnle, P. G.; Collins-Lech, C.: Differentiation of the Effects of Preincubation and Indomethacin on Lymphocyte Transformation. Clin Immunol Immunopathol 13:47–55 (1979).

Tilden, A. B.; Balch, C. M.: Indomethacin enhancement of immunocompetence in melanoma patients. Surgery 90:77–84 (1981).

Toge, T., et al: Correlation between lymphocyte responsiveness to mitogens and results of chemo-immunotherapy in patients with advanced cancer. Gann 70:699–703 (1979).

Tsubono, M., et al: Increased number of suppressor T-cells and impaired IL-2 mediated T-cell function in peripheral blood of gastric cancer patients. J Clin Lab Immunol 33:107–115 (1990).

Vosixa, G.; Thies, J.: Effect of Indomethacin on Blastogenesis of Lymphocytes from Cancer Patients: Differentiation of Patient Types. Clin Immunol Immunopathol 13:30–38 (1979).

Wang, S. R.; Zweiman, B.: Histamine Suppression of Human Lymphocyte Responses to Mitogens. Cell Immunol 36:28–36 (1978).

Watkins, S.: Cancer prognosis predicted by preoperative lymphocyte responsiveness in vitro. Br J Surg 63:433–434 (1976).

Wilhide, C. C.; Larcom, L. L.: An Assay for Monitoring Response to Therapy in Cancer Patients. Ann Clin Lab Sci 23:207–215 (1993).

Zighelboim, J.; Lichtenstein, A.; Benjamin, D.: Response of Normal Subjects to Mitogens. I. Influence of Adherent Cells. Clin Immunol Immunopathol 19:406–415 (1981).

What is claimed is:

1. Method of predicting the therapeutic response of a therapeutic drug directed towards a cancer in a human patient using a sample of blood cells taken from said patient, characterized in that the method comprises the steps of before or shortly after the start of the treatment of said patient with said therapeutic drug taking said sample and culturing blood immunocompetent cells therefrom in a suitable medium;

adding to a first culture of said sample a stimulator of proliferation alone and to a second culture of the same sample said stimulator of proliferation in combination with a immunomodulating substance of said immunocompetent cells, said immunomodulating substance being different from said stimulator of proliferation;

assaying the proliferation of said cells in said cultures; and comparing the proliferation obtained in said first and second cultures in order to demonstrate a correlation between the difference in proliferation of said cells with and without said immunomodulating substance and the therapeutic response of said therapeutic drug directed towards said cancer in human patients, said therapeutic response being a reduction of the tumor size of said cancer and said difference in proliferation of said cells being indicative of the therapeutic response of said therapeutic drug in said human patient.

2. Method as in claim 1, characterized in that said blood immunocompetent cells are blood mononuclear cells.

3. Method as in claim 1, characterized in that said stimulator of proliferation is a mitogen.

4. Method as in claim 1, characterized in that said stimulator of proliferation is a cytokine.

5. Method as in claim 1, characterized in that said immunomodulating substance is indomethacin.

6. Method as in claim 1, characterized in that said immunomodulating substance is chlorambucile.

7. Method as in claim 1, characterized in that said immunomodulating substance is cimetidine.

8. Method as in claim 3, characterized in that said mitogen is concanavalin A (ConA).

9. Method as in claim 3, characterized in that said mitogen is phytohemagglutinin (PHA).

10. Method as in claim 4, characterized in that said cytokine is interleukin-2 (IL-2).

* * * * *